Sept. 5, 1961 | W. FLEMER III | Plant Pat. 2,086
LINDEN TREE
Filed Nov. 7, 1960 | 2 Sheets-Sheet 1
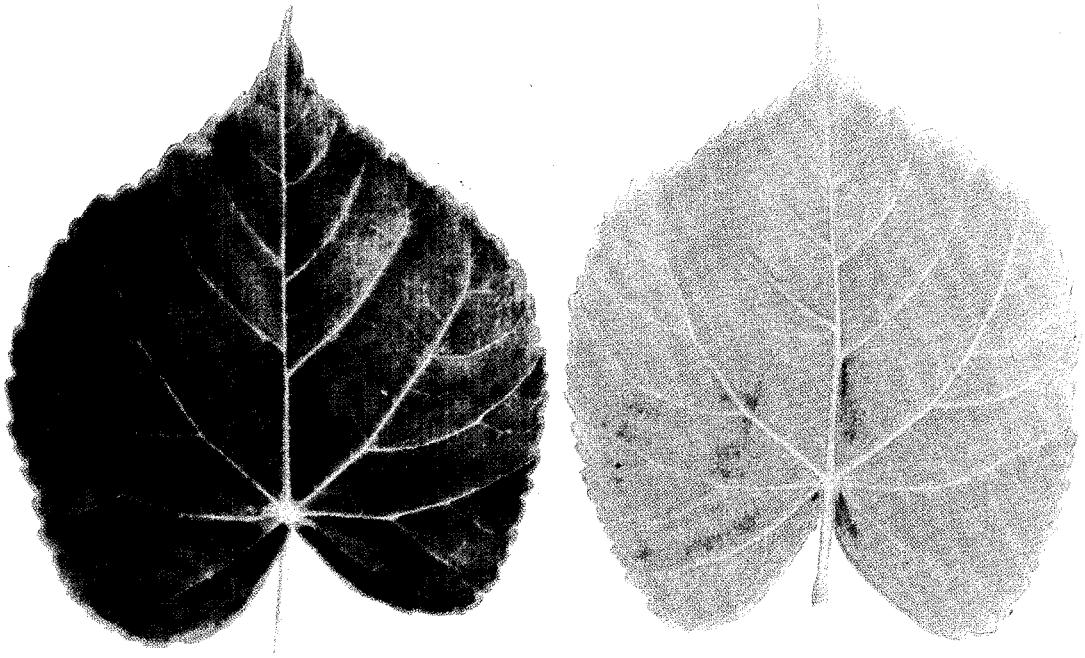
Inventor.
William Flemer III
By: Robb & Robb
Attorneys.

LINDEN TREE
Filed Nov. 7, 1960 2 Sheets-Sheet 2
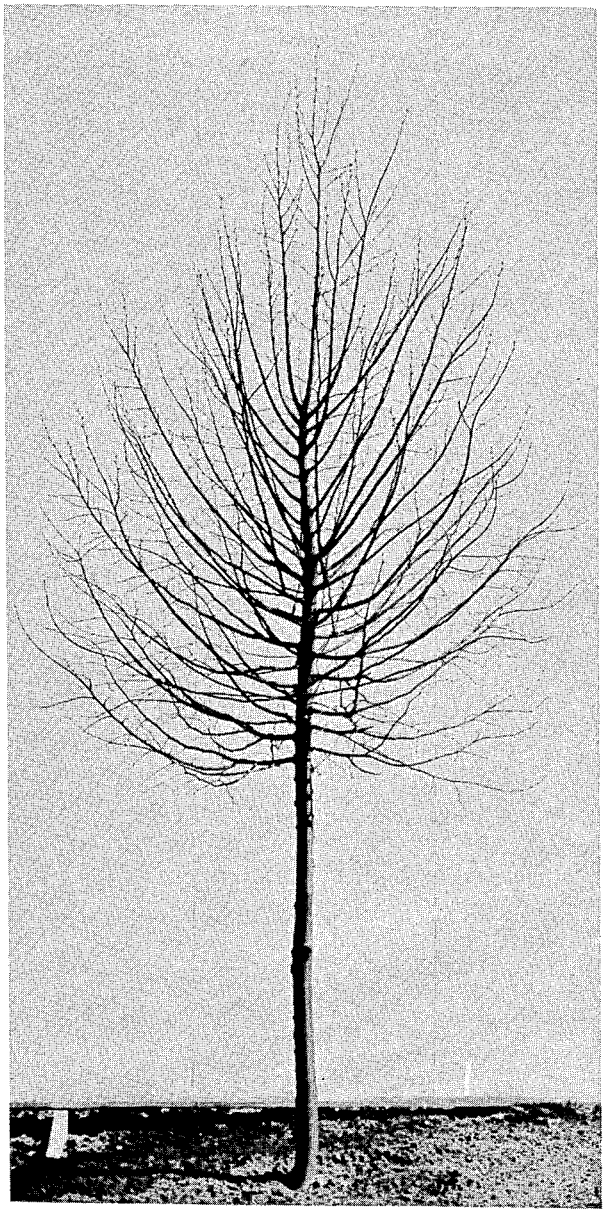
INVENTOR
William Flemer III
BY Robb & Robb
ATTORNEYS United States Patent Office Plant Pat. 2,086
Patented Sept. 5, 1961

2,086
LINDEN TREE

William Flemer III, Princeton, N.J., assignor to Princeton Nurserymen's Research Associates, Princeton, N.J., a partnership Filed Nov. 7, 1960, Ser. No. 67,867
1 Claim. (Cl. 47—59)

The present invention relates to a new and distinct variety of *Tilia cordata* (commonly known as Linden tree), which was originated by me as a selected seedling derived from crossing the variety of *Tilia cordata* named "Boston" (unpatented) and another variety of *Tilia cordata* named "Euclid" (unpatented), the former being the male parent and the latter being the female parent of this cross.

As the result of this breeding, I have produced a new variety of Linden tree which is endowed with the following unique combination of outstanding characteristics which distinguish my new variety from its parents, as well as from all other varieties of which I am aware:

(1) An exceptionally straight and upright habit of growth, even in its early stages, with the result that costly staking is not required, as in the case of other varieties where staking is necessary to achieve straight trunks;

(2) Excellent and attractive green foliage, which is especially resistant to foliar aphids and with the resulting freedom thereof from any "sooty" appearance in late summer which is characteristic of many Linden species;

(3) A symmetrical form of growth, with the branches equally distributed around the trunk, instead of in a single relatively flat plane as is typical of many species;

(4) Strong crotches which are resistant to wind damage and breakage; and (5) Rapid growth, which attains an upright oval form without frequent pruning which is usually necessary to produce a shapely form in the ordinary species of Linden trees.

Asexual reproduction of my new variety of Linden tree, as performed by me by budding (sometimes called bud-grafting), at my nursery in the township of Plainsboro, in the State of New Jersey, shows that the foregoing characteristics and distinctions come true to form and are established and transmitted through succeeding propagations.

The accompanying drawings show typical specimens of the foliage of my new variety, with one view depicting the upper surface thereof and another view the lower surface thereof, as illustrated in color as nearly true as it is reasonably possible to make the same in a color illustration of this character and, in addition, a typical tree, without foliage and which depicts in black and white the general form and branching habit of the tree.

The following is a detailed description of my new variety, with color terminology in accordance with the Munsell Color Chart, except where general color terms of ordinary dictionary significance are obvious:

Parentage: Seedling.
*Male parent.*—"Boston."
*Female parent.*—"Euclid."

Propagation: Holds its distinguishing characteristics through succeeding propagations by budding.

Locality where grown and observed: Princeton, New Jersey.

Tree: Medium size; vigorous; very upright; tall; rapid-growing; hardy.
*Head.*—Conical ovate.
*Trunk.*—Medium stocky. Bark—smooth.
*Branches.*—Medium thickness; much-branched; excurrent pattern. Bark—smooth. Color—Red-Brown, Plate 10.OYR3/2 (value=3, chroma=2).
*Lenticels.*—Moderately abundant; large.

Foliage:
*Leaves.*—Thick, with especially thick cuticle; medium size; suborbicular; almost equally cordate; abruptly acuminate; glabrous; with small axiallary tufts of brown hair. Length along midrib—from 8.5 to 9.5 cm. Width—from 8.0 to 9.5 cm. Margin—sharply serrate; width between serrations about 3 mm.; depth of serrations about 1 mm. Color (mature): upper surface—Moss Green, Plate 2.5GY4/4; under surface—Moderate Yellow-Green, Plate 2.5GY5/2, with Yellow, Plate 2.5GY6/8 veins. Petiole—moderately short; from 2.5 to 3.5 cm. in length; thick.

Flowers: Mid-season, as compared with other varieties; medium small in size; from 5 to 6 per cyme; very fragrant; floral bract from 5 to 6 cm. long. Color—Yellow Green, Plate 2.5GY9/8.

Fruit: Not particularly productive; 4 or 5 per cyme; width about 6 mm.; length about 7 mm.; densely pubescent.

Disease and insect resistance: Average resistance to disease, but especially resistant to attack by foliar aphids, as determined by comparison with other varieties grown under comparable cultural conditions at Princeton, New Jersey; resistance to aphids results in freedom from objectionable "sooty" appearance of the foliage in late summer as occurs with other species.

I claim:

A new and distinct variety of Linden tree (*Tilia cordata*), substantially as herein shown and described, characterized particularly as to novelty by the unique combination of an exceptionally straight and upright habit of growth, even in the young stage, fine and attractive green foliage having especially good resistance to foliar aphids, with attendant absence of any "sooty" appearance in late summer, a symmetrical form with the branches equally distributed around the trunk and forming an upright oval shape without the need of pruning, strong crotches that are resistant to wind damage and breakage, and a rapid habit of growth.

No references cited.